US009057686B2

(12) United States Patent
Fonda et al.

(10) Patent No.: US 9,057,686 B2
(45) Date of Patent: Jun. 16, 2015

(54) NON-DESTRUCTIVE INSPECTION APPARATUS HAVING AN ERGONOMIC GRIP AND ASSOCIATED METHOD

(75) Inventors: James W. Fonda, Moscow Mills, MO (US); Christopher S. Huskamp, St. Louis, MO (US)

(73) Assignee: The Boeing Company, Chicago, IL (US)

( * ) Notice: Subject to any disclaimer, the term of this patent is extended or adjusted under 35 U.S.C. 154(b) by 709 days.

(21) Appl. No.: 13/298,325

(22) Filed: Nov. 17, 2011

(65) Prior Publication Data
US 2013/0125657 A1 May 23, 2013

(51) Int. Cl.
*G01N 29/04* (2006.01)
*G01N 29/265* (2006.01)
*G01N 29/22* (2006.01)

(52) U.S. Cl.
CPC .............. *G01N 29/226* (2013.01); *G01N 29/04* (2013.01); *G01N 29/265* (2013.01); *G01N 2291/044* (2013.01)

(58) Field of Classification Search
CPC . G01N 29/225; G01N 29/226; A61B 8/4455; A61B 8/00; G10K 11/004
USPC ............... 73/632, 602, 431, 432.1, 866.5; 600/446, 445
See application file for complete search history.

(56) References Cited

U.S. PATENT DOCUMENTS

| 5,897,503 | A | 4/1999 | Lyon et al. |
| 7,478,569 | B2 | 1/2009 | Bossi et al. |
| 7,562,576 | B2 | 7/2009 | Fetzer et al. |
| 2006/0173331 | A1* | 8/2006 | Booton et al. ............... 600/445 |

(Continued)

FOREIGN PATENT DOCUMENTS

EP  1 935 343 A1  6/2008

OTHER PUBLICATIONS

Ultrasonic Flaw Detectors and Ultrasonic Thickness Gauges and NDT Transducers for N . . . [online] [retrieved Oct. 24, 2014]. Retrieved from the Internet: <URL: http://web.archive.org/web/20111028051154/http://ndtsystems.com/>. (2001-2011) 3 pages.

(Continued)

*Primary Examiner* — Laura Martin
*Assistant Examiner* — Rose M Miller
(74) *Attorney, Agent, or Firm* — Alston & Bird LLP

(57) ABSTRACT

A non-destructive inspection apparatus, system and associated method are provided to facilitate the inspection of a workpiece. The non-destructive inspection apparatus includes an ultrasonic sensor configured to be placed in operable contact with the workpiece. The ultrasonic sensor is configured to emit ultrasonic signals into the workpiece and to receive return signals from the workpiece. The non-destructive inspection apparatus also includes a grip operably connected to the ultrasonic sensor such that the grip and the ultrasonic sensor are movable in concert. The grip is configured to support an operator's palm, such as a majority of the operator's palm, such that force applied to the ultrasonic inspection apparatus by the operator is transferred via the grip to the ultrasonic sensor. The non-destructive inspection system may also include a computer in communication with the non-destructive inspection apparatus to receive information relating to the return signals received by the ultrasonic sensor.

23 Claims, 5 Drawing Sheets

(56) References Cited

U.S. PATENT DOCUMENTS

2009/0126494 A1* 5/2009 Karasawa et al. ............... 73/620
2010/0212429 A1* 8/2010 Isobe et al. ...................... 73/602

OTHER PUBLICATIONS

GE Reveals Phone-Sized Ultrasonic Device | Singularity Hub [online] [retrieved Oct. 24, 2014]. Retrieved from the Internet: <URL: http://web.archive.org/web/20110830194032/http://singularityhub.com/2009/11/04/ge-re...>. (dated Nov. 4, 2009) 5 pages.

Sonatest :: Home [online] [retrieved Oct. 24, 2014]. Retrieved from the Internet: >URL: http://web.archive.org/web/20111107105855/http://ww.sonatest.com/>. (2011); also [online] [retrieved Oct. 23, 2014]. Retrieved from the Internet: <URL: http://sonatest.com/> (2014) 2 pages.

Extended European Search Report for corresponding European Application No. 12192219.9 date Feb. 25, 2015, 5 pages.

* cited by examiner

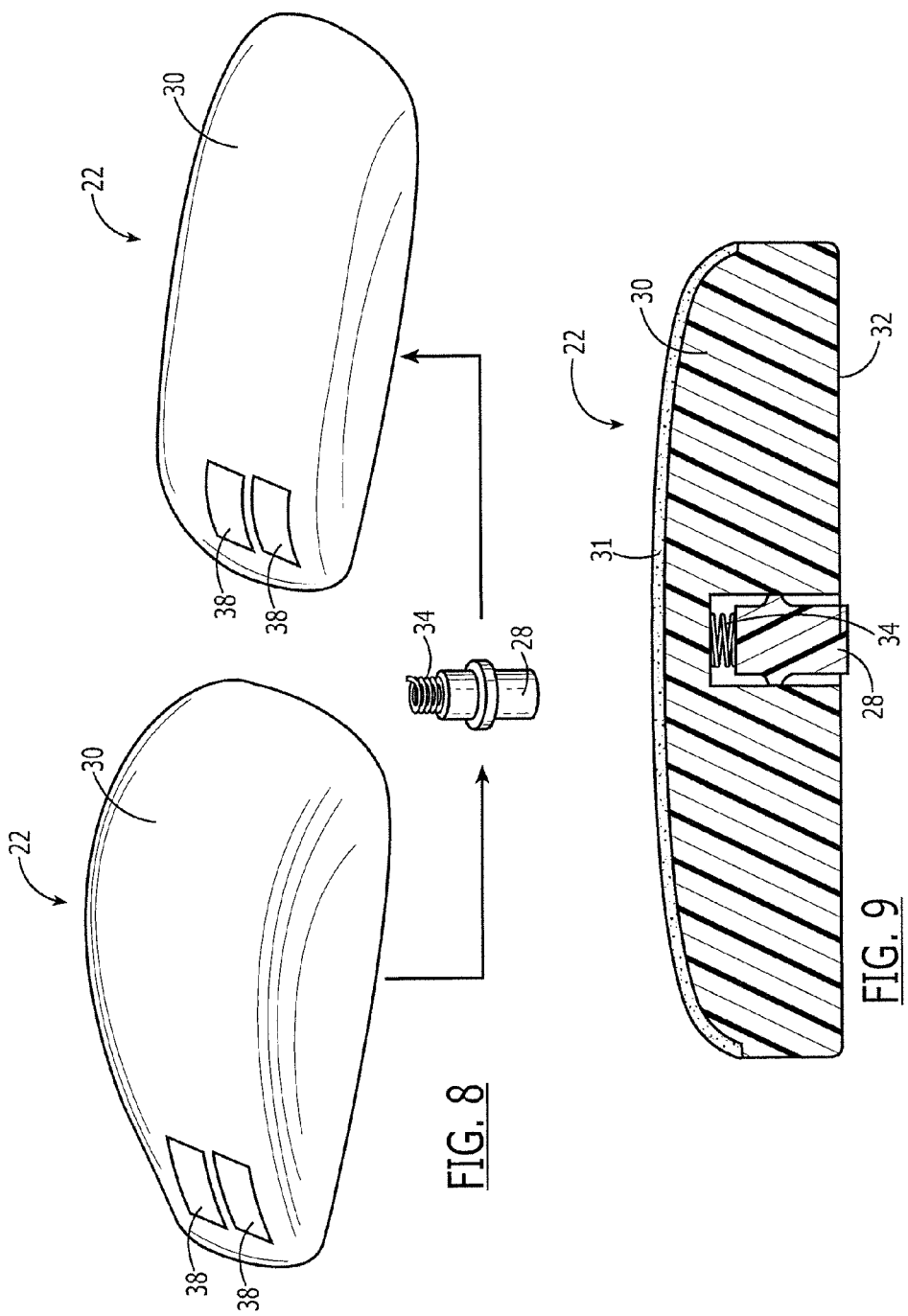

NON-DESTRUCTIVE INSPECTION APPARATUS HAVING AN ERGONOMIC GRIP AND ASSOCIATED METHOD

TECHNOLOGICAL FIELD

An example embodiment of the present disclosure relates generally to a non-destructive inspection apparatus and associated method and, more particularly, to a non-destructive inspection apparatus having an ergonomic grip and an associated method.

BACKGROUND

A variety of workpieces are subjected to non-destructive inspection in order to determine various characteristics of the workpiece. For example, various structural panels, such as wings, fuselage sections and the like, may be subjected to non-destructive inspection. A non-destructive inspection apparatus generally includes a sensor that is configured to emit signals into the workpiece and to receive return signals in response to the signals emitted by the sensor. The sensor of a non-destructive inspection apparatus may be, for example, an ultrasonic sensor configured to emit and to receive ultrasonic signals.

In operation, a sensor may be positioned upon a workpiece. The sensor may then be actuated so as to emit signals into the workpiece and to receive return signals from the workpiece in response to the signals emitted by the sensor. By analyzing the return signals, various characteristics of the workpiece may be determined including, for example, the thickness of the workpiece and/or any anomalies that may exist within the portion of the workpiece that is being interrogated. By moving the sensor across the workpiece and interrogating the workpiece at each of a plurality of positions, the non-destructive inspection apparatus may effectively inspect a substantial portion of a workpiece.

Some non-destructive inspection apparatuses include a sensor that is manually placed upon the workpiece and then manually repositioned across the workpiece in order to interrogate a substantial portion of the workpiece. As such, an operator must generally grasp the sensor and then repeatedly reposition the sensor at a number of positions across a workpiece. In order to provide for effective coupling of the sensor with the workpiece and, more particularly, the signals emitted by the sensor and the return signals received from the workpiece, the operator may also exert a force intended to press the sensor against the surface of the workpiece. As a result, the placement and movement of a sensor generally requires some exertion on the part of the operator. The effort expended by the operator is generally compounded by the relatively small size of the sensor. As shown in FIG. 1, for example, an ultrasonic sensor 10 is generally quite small, such as smaller than one of the operator's fingers. As a result, an operator may find the sensor somewhat difficult to grasp and, more particularly, may find it challenging to not only grasp the sensor but to apply the force necessary to urge the sensor into contact with the underlying workpiece.

The challenges that an operator faces in terms of grasping the sensor and applying the desired force to the workpiece may sometimes be compounded by the repetitive motion incurred as the operator places the sensor upon and moves the sensor across a workpiece. Additionally, the operator may be forced to assume a relatively uncomfortable pose while handling the inspection device since the workpiece may be relatively large and may require the operator to reach across at least a portion of the workpiece in order to properly place the sensor and to interrogate the corresponding portion of the workpiece.

BRIEF SUMMARY

A non-destructive inspection apparatus, system and associated method are provided in accordance with an example embodiment in order to facilitate the non-destructive inspection of a workpiece. In this regard, the non-destructive inspection system and the associated method of one embodiment may be configured so as to permit an operator to interact with the non-destructive inspection apparatus in a manner that is more ergonomic, such as by reducing or eliminating any requirement to grasp a relatively small sensor and to apply force upon the sensor so as to ensure operable contact between the sensor and the underlying workpiece. As such, the non-destructive inspection apparatus and associated method may allow the operator to repeatedly position a sensor upon a workpiece and to move the sensor across the workpiece with reduced exertion by the operator.

In one embodiment, a non-destructive inspection apparatus is provided in accordance with one embodiment including an ultrasonic sensor configured to be placed in operable contact with a workpiece. The ultrasonic sensor is configured to emit ultrasonic signals into the workpiece and to receive return signals in response to the ultrasonic signals emitted thereby. The non-destructive inspection apparatus also includes a grip operably connected to the ultrasonic sensor such that the grip and the ultransonic sensor are movable in concert. The grip is configured to support an operator's palm, such as a majority of the operator's palm, such that force applied to the ultrasonic inspection apparatus by the operator is transferred via the grip to the ultrasonic sensor.

A non-destructive inspection apparatus of one embodiment may include a plurality of grips configured to conform to the palm of different respective operators. In this regard, the plurality of grips may be interchangeably connected to the ultrasonic sensor. Additionally or alternatively, the grip may include a gel pad configured to conform to the operator's palm. The non-destructive inspection apparatus of one embodiment may also include a source of spring loading to facilitate coupling of the ultrasonic sensor with the workpiece. The grip of one embodiment may include at least one input element configured to be actuated by the operator. The non-destructive inspection apparatus may also include a suction device operably connected to the ultrasonic sensor and the grip and configured to temporarily affix the ultrasonic sensor to the workpiece.

The non-destructive inspection apparatus may include a communication interface configured to communicate with a positioning system to identify a location to be inspected. The communication interface of one embodiment may be configured to receive positioning signals that define the location of the non-destructive inspection apparatus. In another embodiment, the communication interface may be configured to receive a marker indicative of the location to be inspected.

In another embodiment, a non-destructive inspection system is provided that includes a non-destructive inspection apparatus and a computer in communication with the non-destructive inspection apparatus. The non-destructive inspection apparatus of this embodiment include an ultrasonic sensor configured to be placed in operable contact with a workpiece. The ultrasonic sensor is configured to emit ultrasonic signals into the workpiece and to receive return signals in response to the ultrasonic signals emitted thereby. The non-destructive inspection apparatus of this embodiment also includes a grip operably connected to the ultrasonic sensor such that the grip and the ultransonic sensor are movable in concert. The grip is configured to support an operator's palm, such as the majority of the operator's palm. Additionally, the grip includes at least one input element and, in one embodiment, a plurality of input elements configured to be actuated by the operator. In accordance with this embodiment, the computer is configured to receive information relating to the return signals received by the ultrasonic sensor.

The non-destructive inspection apparatus of one embodiment further includes a plurality of grips configured to conform to the palm of different respective operators. The plurality of grips are interchangeably connected to the ultrasonic sensor. Additionally or alternatively, the grip may include a gel pad configured to conform to the operator's palm. The non-destructive inspection apparatus of one embodiment may also include a source of spring loading to facilitate coupling of the ultrasonic sensor with the workpiece. The non-destructive inspection apparatus may also include a suction device operably connected to the ultrasonic sensor and the grip and configured to temporarily affix the ultrasonic sensor to the workpiece.

The non-destructive inspection apparatus may include a communication interface configured to communicate with a positioning system to identify a location to be inspected. For example, the communication interface may be configured to receive positioning signals that define the location of the non-destructive inspection apparatus. Alternatively, the communication interface may be configured to receive a marker indicative of the location to be inspected.

In a further embodiment, a method for non-destructively inspecting a workpiece includes placing an ultrasonic sensor in operable contact with the workpiece and supporting an operator's palm with a grip that is operably connected to the ultrasonic sensor. The method also includes emitting ultrasonic signals from the ultrasonic sensor into the workpiece and receiving return signals in response to the ultrasonic signals emitted thereby. The method also includes moving the grip and the ultransonic sensor in concert in response to force applied to the grip by the operator is transferred via the grip to the ultrasonic sensor. In one embodiment, the information relating to the return signals may be provided to a computer.

The method of one embodiment may include replacing the grip with another grip configured to conform to the palm of a different operator. The placement of the ultrasonic sensor in operable contact with the workpiece may include spring loading the ultrasonic sensor to facilitate coupling of the ultrasonic sensor with the workpiece. In an embodiment in which the grip includes an input element, the method may also include receiving an indication from the input element regarding actuation of the input element by the operator. The method of one embodiment may also include temporarily affixing the ultrasonic sensor to the workpiece while emitting ultrasonic signals and receiving return signals.

The method may also include communicating with a positioning system to identify a location to be inspected. In this regard, the communications with the positioning system may include receiving positioning signals that define the location of the non-destructive inspection apparatus. Alternatively, the communications with the positioning system may include receiving a marker indicative of the location to be inspected.

The features, functions and advantages that have been discussed can be achieved independently in various embodiments of the present disclosure or may be combined in yet other embodiments, further details of which can be seen with reference to the following description and drawings.

BRIEF DESCRIPTION OF THE SEVERAL VIEWS OF THE DRAWINGS

Figure 1:
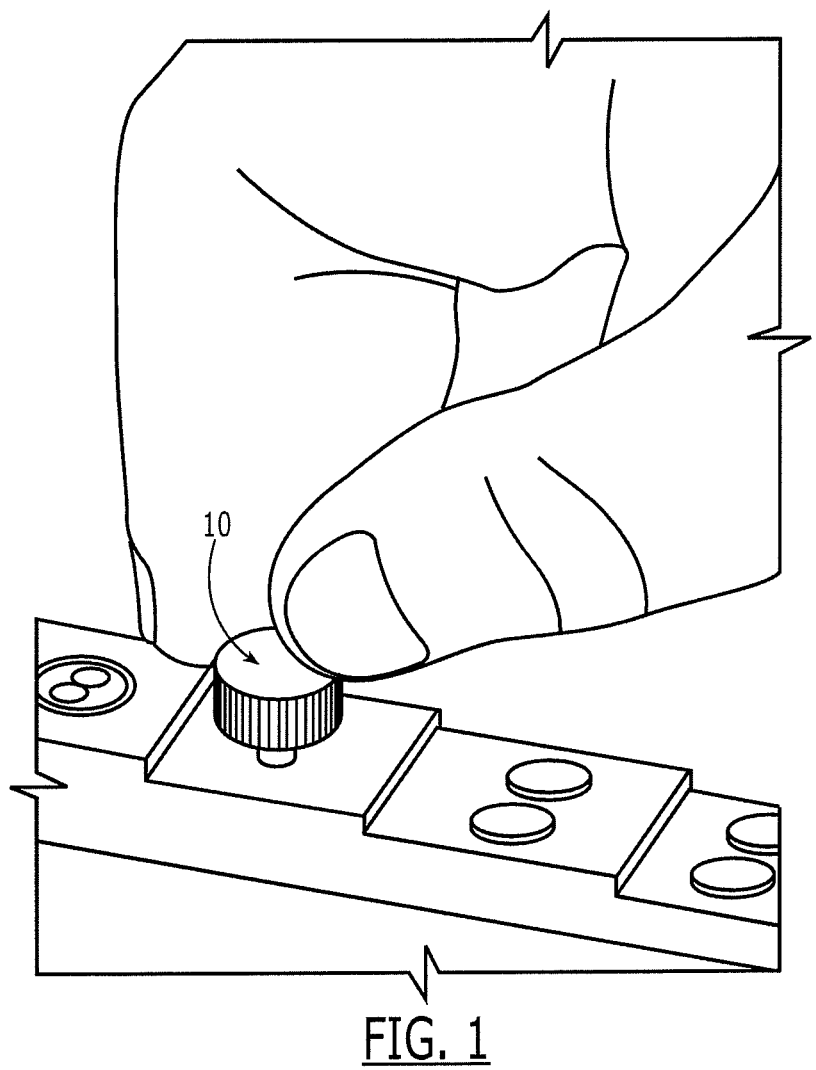
Figure 2:
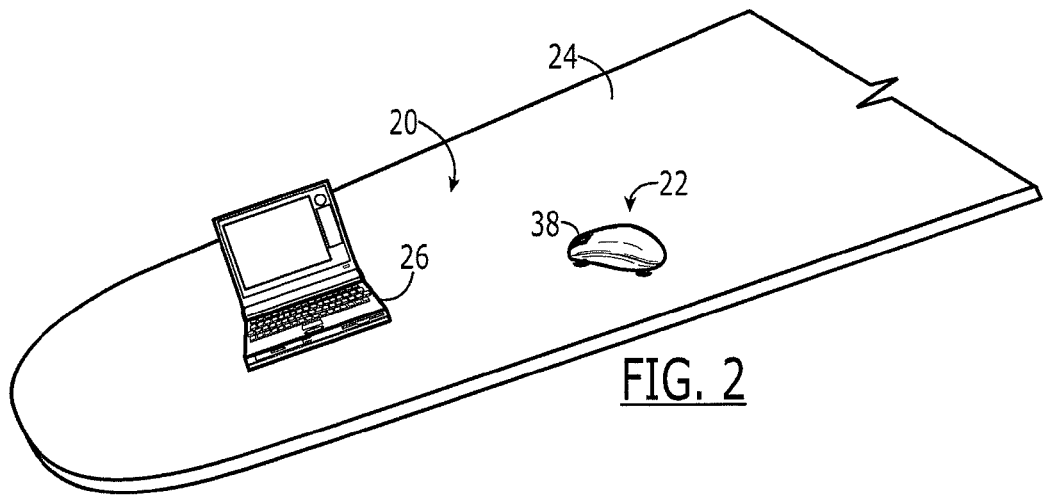
Figure 3:
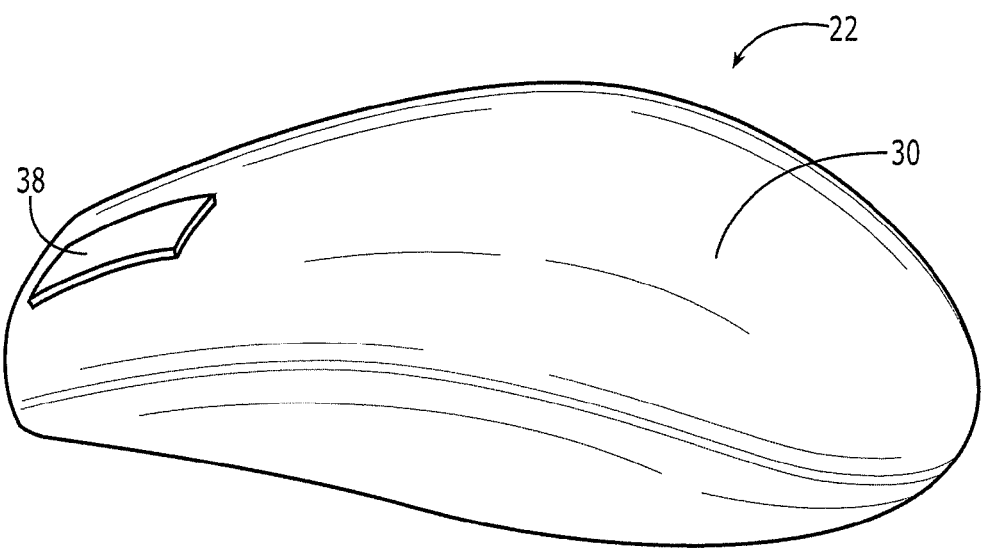
Figure 4:
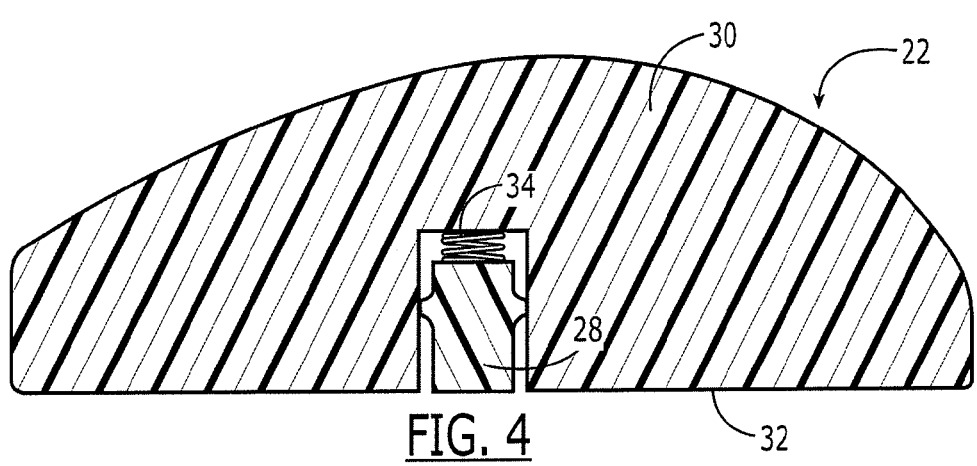
Figure 5:
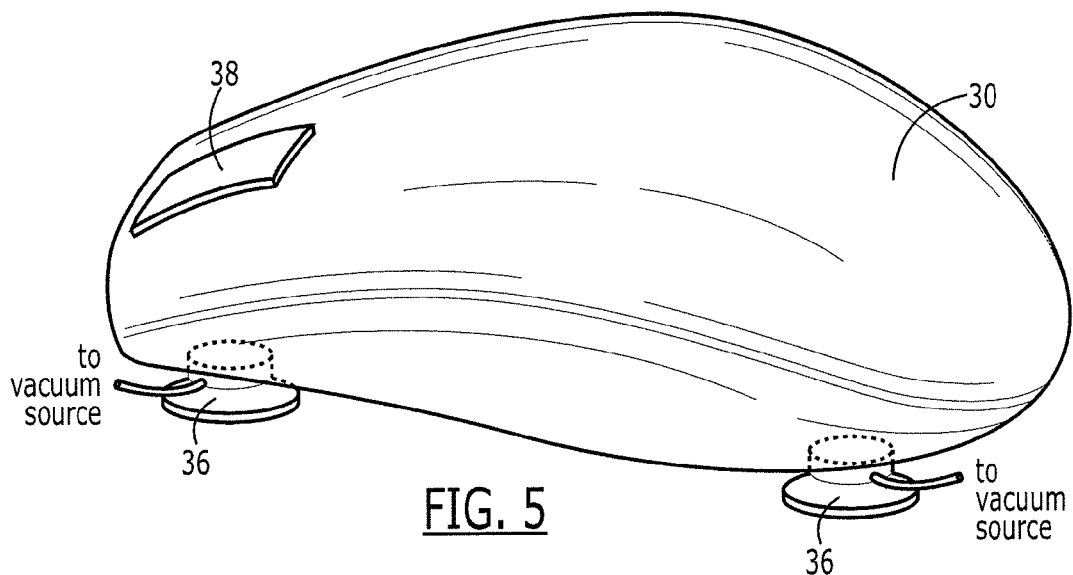
Figure 6:
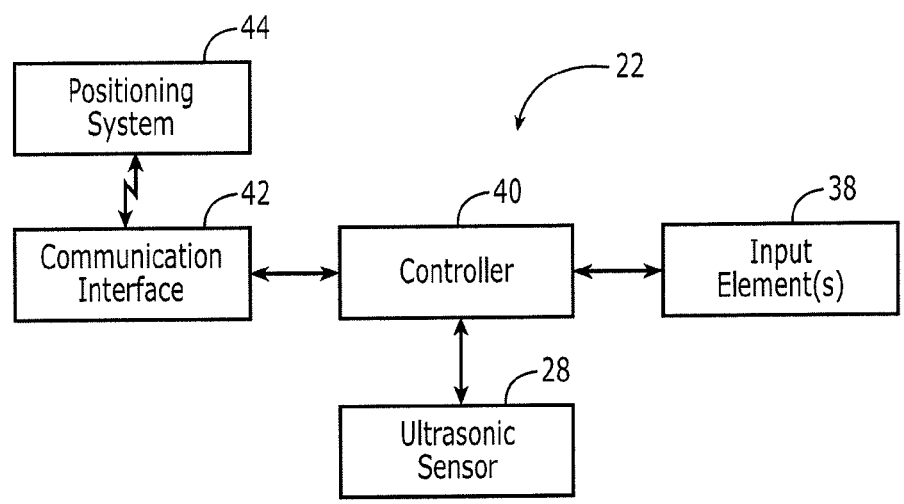
Figure 7:
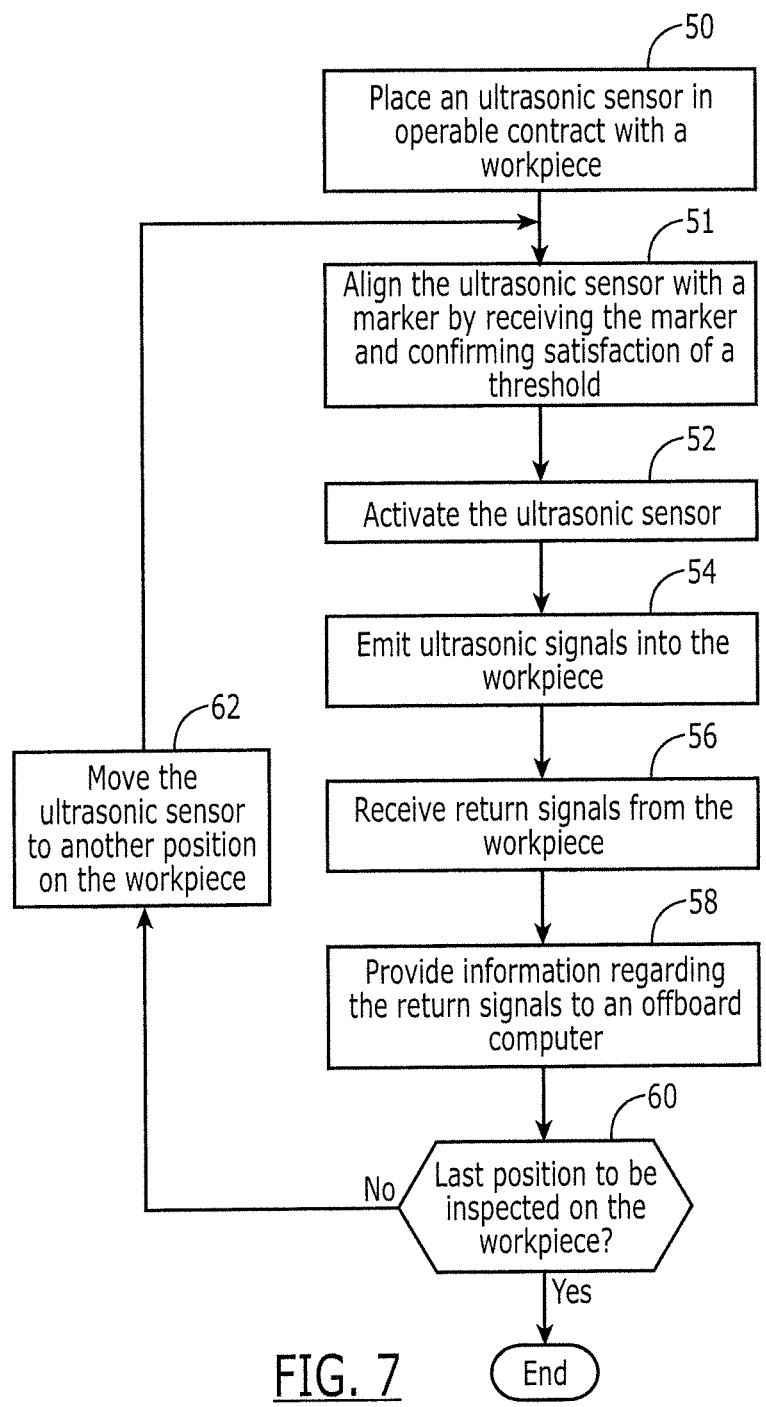

Having thus described example embodiments of the present disclosure in general terms, reference will now be made to the accompanying drawings, which are not necessarily drawn to scale, and wherein:

FIG. 1 is a perspective view of a conventional non-destructive inspection sensor;

FIG. 2 is a perspective view of a non-destructive inspection system in accordance with one embodiment of the present disclosure;

FIG. 3 is a perspective view of a non-destructive inspection apparatus in accordance with one embodiment of the present disclosure;

FIG. 4 is a cross-sectional view of the non-destructive inspection apparatus of FIG. 3;

FIG. 5 is a side view of a non-destructive inspection apparatus of another embodiment of the present disclosure;

FIG. 6 is a block diagram of a non-destructive inspection apparatus of one embodiment of the present disclosure;

FIG. 7 is a flowchart illustrating operations performed in accordance with a method for non-destructively inspecting a workpiece in accordance with an example embodiment of the present disclosure;

FIG. 8 illustrates a pair of alternative grips between which an ultrasonic sensor may be interchanged in accordance with an example embodiment of the present disclosure; and FIG. 9 is a side cross-sectional view of a grip that includes a gel pad in accordance with an example embodiment of the present disclosure.

DETAILED DESCRIPTION

The present disclosure now will be described more fully hereinafter with reference to the accompanying drawings, in which some, but not all embodiments are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

Referring now to FIG. 2, a non-destructive inspection system 20 in accordance with one embodiment is depicted. As shown, the non-destructive inspection system 20 includes a non-destructive inspection apparatus 22 including a sensor that is placed in operable contact with a workpiece 24 in order to interrogate the workpiece and to provide information from which one or more characteristics of the workpiece may be determined. The non-destructive inspection apparatus 22 may be configured to be manually positioned upon the workpiece 24 and to then be manually moved across the workpiece so as to interrogate the workpiece at each of a plurality of different positions. For example, the non-destructive inspection apparatus 22 may be configured to be initially placed at a predetermined position upon the workpiece 24 and to thereafter be moved in a predefined pattern across a workpiece so as to interrogate the workpiece at each of a plurality of predefined positions.

Various types of workpieces 24 may be subjected to non-destructive inspection. In regards to the example embodiment of FIG. 2, at least a portion of a wing is subjected to non-destructive inspection. However, a number of other types of workpieces 24 may be subjected to non-destructive inspection including other components of an aircraft or other vehicle, structural components of buildings or other structures and the like. Additionally, the workpiece 24 to be inspected may be a composite structure. However, the workpiece 24 to be inspected may alternatively be constructed in other fashions.

While the non-destructive inspection apparatus 22 may be placed in direct contact with the workpiece 24, the non-destructive inspection system may include a couplant that is applied to at least a portion of the workpiece that is to be inspected such that the non-destructive inspection apparatus and, at least the sensor of the non-destructive inspection apparatus, is spaced from the surface of the workpiece by the couplant The couplant may be configured to facilitate coupling between the sensor and the workpiece 24, thereby increasing the efficiency with which the signals emitted by the sensor propagate into the workpiece 24 and the return signals from the workpiece propagate to the sensor. While various types of couplants may be utilized, examples of suitable couplants include ultrasonic gels and water.

In addition to the non-destructive inspection apparatus 22, the non-destructive inspection system 20 may include a computer 26 as shown in FIG. 2. The non-destructive inspection system 20 may include various types of computer 26 including, without limitation, personal computers, laptop computers, tablet computers and mobile devices including mobile phones, personal digital assistants (PDAs) and the like. The computer 26 is in communication with the non-destructive inspection apparatus 22. While the non-destructive inspection apparatus 22 and the computer 26 may be configured to communicate with one another wirelessly, the non-destructive inspection apparatus and the computer may be configured for wired communication in other embodiments. As described below, the computer 26 may be configured to receive information from the non-destructive inspection apparatus 22 and to process, display and/or store the information in order to facilitate the inspection of the workpiece 24.

The workpiece 24 may be inspected so as to identify various different characteristics of the workpiece. In this regard, the non-destructive inspection apparatus 22 may inspect the workpiece 24 so as to determine the thickness of the workpiece. In this regard, the non-destructive inspection apparatus 22 may emit signals into the workpiece 24 and may detect return signals that have reflected from an opposed surface of the workpiece such that the thickness of the workpiece may be determined based upon the elapsed time between the emission of the signals into the workpiece and the receipt of the return signals. Additionally or alternatively, the non-destructive inspection apparatus 22 may be configured to detect anomalies within the workpiece 24 by emitting signals into the workpiece and receiving return signals that are indicative of the presence or absence of an anomaly within the portion of the workpiece being interrogated.

A non-destructive inspection apparatus 22 in accordance with one embodiment of the present disclosure is shown in perspective in FIG. 3 and in cross-section in FIG. 4. In this regard, the non-destructive inspection apparatus 22 may include an ultrasonic sensor 28, such as an ultrasonic transducer, configured to be placed in operable contact with the workpiece 24. As described above, the ultrasonic sensor 28 may be placed in direct contact with the workpiece 24 or may be spaced apart from the workpiece by a couplant. The ultrasonic sensor 28 of this embodiment is configured to emit ultrasonic signals into the workpiece 24 and to receive return signals in response to the ultrasonic signals emitted thereby. While the ultrasonic sensor 28 of the illustrated embodiment may be embodied as a transducer that is configured to both emit ultrasonic signals and to receive return signals, the ultrasonic sensor may, in other embodiments, be embodied by an ultrasonic transmitter that is configured to emit ultrasonic signals into the workpiece 24 and a distinct or separate ultrasonic receiver that is configured to receive the return signal from the workpiece in response to the ultrasonic signals emitted by the ultrasonic transmitter.

In contrast to the non-destructive inspection apparatus of FIG. 1 in which an operator must directly grasp the ultrasonic sensor 10, the non-destructive inspection apparatus 22 of the illustrated embodiment also includes a grip 30 that is operably connected to the ultrasonic sensor 28. In this regard, the grip 30 may be directly connected to the ultrasonic sensor. In one embodiment shown, for example, in FIGS. 3 and 4, the ultrasonic sensor 28 may be embedded within the grip 30 so as to be exposed through and positioned proximate to the surface 32 of the grip that is placed in operable contact with the workpiece 24. As described below, for example, the grip 30 of this embodiment may define a cavity in which the inspection sensor 28 is disposed and frictionally engaged. In other embodiments, however, the grip 30 may be connected to the ultrasonic sensor 28 in other manners so that, for example, the ultrasonic sensor is external to the grip. In any instance, the grip 30 and the ultrasonic sensor 28 are operably connected so that both the grip and the ultrasonic sensor are movable in concert. As such, movement of the grip 30 relative to the workpiece 24 causes the ultrasonic sensor 38 to move in a corresponding fashion.

The grip 30 of the non-destructive inspection apparatus 22 is configured to support the palm of an operator's hand and, in one embodiment, is configured to support the majority of the operator's palm. As such, the operator may apply force to the non-destructive inspection apparatus 22 as a result of the interaction of the operator's hand with the grip 30 such that the force applied by the operator is transmitted via the grip to the ultrasonic sensor 28. In this regard, the operator may apply force during the initial positioning of the non-destructive inspection apparatus 22 and during subsequent movement of the non-destructive inspection apparatus relative to the workpiece 24. Additionally, the operator may apply force via the grip 30 to the ultrasonic sensor 28 during the actuation of the ultrasonic sensor, that is, during the emission of ultrasonic signals into the workpiece 24 and receipt of return signals from the workpiece. In this instance, the operator may apply force that is directed toward the workpiece 24 so as to increase the likelihood that the non-destruction inspection apparatus 22 is effectively coupled to the workpiece. By the supporting the palm of an operator's hand, the grip of the non-destructive inspection apparatus 22 may be more ergonomic in that the operator will find interaction with the non-destructive inspection apparatus to require less effort and to impose less strain thereupon than a conventional ultrasonic sensor 10 as shown in FIG. 1 in which the operator must grasp the ultrasonic sensor iteself. As such, an operator may be able to utilize a non-destructive inspection apparatus 22 repeatedly and for longer periods of time without subjecting the operator to undesired levels of exertion or exhaustion.

The grip 30 of one embodiment may be formed of a soft material and configured to conform to the palm of the operator's hand. In this regard, the non-destructive inspection apparatus 22 may include a plurality of different grips, each of which has been formed in order to conform to the palm of a respective operator. In this embodiment, the non-destructive inspection apparatus 22 may be configured such that the plurality of grips 30 are interchangeable. As such, prior to use, an operator may select the grip 30 that has been configured to conform to the palm of the operator's hand and may replace another grip that was previously operably connected to the ultrasonic sensor 28 with the grip that is configured to conform to the palm of the respective operator's hand. The grips 30 of this embodiment may be removably attached to the ultrasonic sensor 28 in various manners.

In one embodiment, however, the grip 30 may define a cavity sized to frictionally receive the ultrasonic sensor 28. The cavity may open through the surface 32 of the grip 30 that is intended to face the workpiece 24. In order to interchange grips 30, the ultrasonic sensor 28 may be disengaged from the cavity of a prior grip and may be inserted and frictionally engaged within the cavity of another grip that is configured to conform to the palm of the respective operator's hand. See, for example, FIG. 8 in which the ultrasonic sensor 28 is interchanged between two different grips. Although an ultrasonic sensor 28 may be retained within a grip 30 by frictional forces, the ultrasonic sensor may be operably connected to the grip by other mechanisms in other embodiments.

In addition to or as an alternative to having a plurality of grips 30, each of which has been configured to conform to the palm of a respective operator's hand, the grip may include a gel pad 31 that conforms to the palm of each operator's hand. See FIG. 9. In this embodiment, the gel pad may at least partially protect the operator from vibration and impact that may otherwise be incurred during use. Additionally, the gel pad may evenly distribute the forces across the palm of the operator's hand as well as across the grip 30 so as to further reduce the strain upon the operator and to provide for more even force distribution across that portion of the workpiece 24 upon which the non-destructive inspection apparatus 22 is positioned.

In order to further insure that the non-destructive inspection apparatus 22 makes consistent contact with the workpiece 24, either directly or via the couplant that may coat the workpiece, the non-destructive inspection apparatus 22 and, more particularly, the ultrasonic sensor 28 may also be spring loaded. As shown, for example, in the cross-sectional view of FIG. 4, the source of the spring loading may be a spring 34 such as a helical spring. Alternatively, the non-destructive inspection apparatus 22 may include a foam for providing the spring loading to maintain normal contact with the workpiece 24 and to facilitate coupling of the ultrasonic sensor 28 with the workpiece.

In order to further facilitate coupling of the ultrasonic sensor 28 with the workpiece 24, the non-destructive inspection apparatus 22 of one embodiment may also include one or more suction devices 36, such as suction cups, as shown in FIG. 5. In this regard, the suction device 36 may be configured to temporarily affix the non-destructive inspection apparatus 22 to the workpiece 24. In one embodiment, the suction device 36 includes a suction cup and the non-destructive inspection system 20 may further include a vacuum source coupled to the suction cup via a one-way valve for drawing a vacuum or at least a partial vacuum between the suction cup and the workpiece 24, thereby temporarily affixing the non-destructive inspection apparatus 20 to the workpiece in a manner that both maintains the position of the inspection sensor 28 and applies a constant pressure across the inspection sensor. Once it is determined that the non-destructive inspection apparatus 22 has completed the interrogation of the workpiece 24 at its current location and is ready to be moved, the vacuum may be released, such as by actuation of a pressure release valve, and the non-destructive inspection apparatus may be moved relative to the workpiece.

As shown in FIGS. 3 and 5, the grip 30 may include one or more input elements 38 that are configured to be actuated by the operator. As shown, the input elements 38 may include a plurality of buttons responsive to user input for actuation. However, the input element(s) 38 may be configured in a number of other manners so long as the input element(s) are responsive to actuation by the operator. The input element(s) 38 may be configured to interpret the actuation in different manners depending upon the manner in which the non-destructive inspection apparatus 22 is configured. For example, actuation of an input element 38 may cause the ultrasonic sensor 28, in turn, to be actuated. In this regard, once an operator has properly positioned the non-destructive inspection apparatus 22 upon the workpiece 24, the operator may actuate one of the input elements 38 in order to cause the ultrasonic sensor 28 to emit the ultrasonic signals into the workpiece and to receive the return signals therefrom. Additionally or alternatively, the actuation of an input element 38 may cause the non-destructive inspection apparatus 22 to transmit information relating to the return signals to a computer 26, such as for processing, display and/or storage.

By way of further explanation, FIG. 6 is a block diagram of one embodiment of a non-destructive inspection apparatus 22. In this embodiment, the non-destructive inspection apparatus 22 may include a controller 40 configured to receive input from the operator via the input elements 38. Additionally, the controller 40 may be configured to communicate with the ultrasonic sensor 28, such as to actuate the ultrasonic sensor in response to actuation of a respective input element 38 and to receive a representation of the return signals from the ultrasonic sensor. The non-destructive inspection apparatus 22 of this embodiment may also include a communications interface 42 including, for example, a transmitter for transmitting information relating to the return signals to the computer 26, such as via a wired or wireless connection.

As shown in FIG. 7, a method for the non-destructive inspection of a workpiece 24 may include placing an ultrasonic sensor 28 in operable contact with the workpiece. See operation 50. In one embodiment, the ultrasonic sensor 28 may initially be placed at a predefined position, such as a starting position, upon a workpiece 24. During the placement of the non-destructive inspection apparatus 22 upon the workpiece 28, the palm of the operator's hand may be supported by the grip 30 so as to permit the operator to handle the non-destructive inspection apparatus in a more ergonomic fashion. The method of this embodiment may also emit ultrasonic signals from the ultrasonic sensor 28 into the workpiece 24 while the ultrasonic sensor is positioned at the respective position, such as the starting position. See operation 54. In one embodiment, the operator may actuate an input element 38 of the grip 30 in order to cause the controller 40 to trigger the emission of the ultrasonic signals from the ultrasonic sensor 28 into the workpiece 24. See operation 52. In response to the ultrasonic signals emitted by the ultrasonic sensor 28, the ultrasonic sensor may receive the return signals. See operation 56. While the return signals may be stored, processed and the like onboard the non-destructive inspection apparatus 22, the non-destructive inspection apparatus of one embodiment may be configured to provide information relating to the return signals to a computer 26, such as via wireless communications, to facilitate offboard processing, storage and/or display of information relating to the return signals by the computer. See operation 58. In this regard, the operator may actuate an input element 38 of the grip 30 in order to cause the controller 40 to trigger the communications interface 42 to transmit the information relating to the return signals to the computer 26. The information relating to the return signals may relate to various characteristics of the workpiece 24 including the thickness of the workpiece, anomalies within the portion of the workpiece under inspection and the like.

Once the workpiece 24 has been inspected at a first predetermined position, such as at the starting position, a determination may be made as to whether there are other portions of the workpiece that remain to be inspected. See operation 60. In an instance in which other portions of the workpiece 24 remain to be inspected, the operator may apply force to the grip 30 so as to move the grip and the ultrasonic sensor 28 in concert to a second position on the same workpiece or on a different workpiece. See operation 62 of FIG. 7. This process may then be repeated for each of a plurality of different positions upon the workpiece 24 so as to thoroughly inspect a workpiece by moving the ultrasonic sensor along a predefined path and interrogating the workpiece at each of the plurality of positions along, for example, a predefined inspection path. At each position, the ultrasonic sensor 28 may receive the return signals and the non-destructive inspection apparatus 22 may provide information regarding return signals to the computer 26, either following receipt of the return signals at each position or in a batch form following the receipt of the return signals for all or at least a plurality of positions across the workpiece. By permitting an operator to interact with a non-destructive inspection apparatus 22 by means of a grip 30 that supports the palm, such as a majority of the palm, of the operator's hand, the non-destructive inspection apparatus of an example embodiment provides an ergonomic device for reducing operator exertion and exhaustion, thereby permitting an operator to repetitively utilize the non-destructive inspection apparatus for longer periods of time than in instances in which the operator had to grasp a much smaller ultrasonic sensor 10 as shown in FIG. 1.

As described above, the non-destructive inspection apparatus 22 may be manually moved across a workpiece 24 so as to inspect the workpiece at a plurality of locations. The operator may identify the locations to be inspected. Alternatively, the non-destructive inspection apparatus 22 may communicate with a positioning system 44 as shown in FIG. 6 in order to identify the locations to be inspected. The positioning system 44 may be embodied in various manners. In one embodiment, however, the positioning system 44 includes a plurality of global positioning system (GPS) satellites or a plurality of pseudolites, such as a plurality of transceivers positioned about the facility in which the inspection is being performed. The positioning system 44 of this embodiment is in communication with the communication interface 42 of the non-destructive inspection apparatus 22 so as to provide positioning signals that may be processed by the controller 40 or by a positioning module, such as a GPS module, that is in communication with the controller. Based upon the positioning signals, the controller 40 or an associated positioning module may determine the location of the non-destructive inspection apparatus 22. As such, the communication interface 42 of this embodiment may not only provide information relating to the return signals to the computer 26, but may also identify the location at which the return signals were captured based upon the positioning signals provided by the positioning system 44.

In another embodiment, the positioning system 44 may include a projector, such as a laser projector, for illuminating the workpiece 24 with one or more markers, such as illuminated dots. In this regard, the positioning system 44, such as the projector, may be initially aligned and calibrated with the workpiece 24 such that the markers with which the workpiece is illuminated indicated locations to be inspected. In order to inspect the workpiece 24 at one of the locations identified by a marker, the non-destructive inspection apparatus 22 may be moved into alignment with the marker. In order to confirm alignment, the communication interface 42 may include a receiver, such as a photodiode and, in one embodiment, a lens, in order to receive the marker, such as a laser signal, provided by the positioning system 44. Once the receiver receives the marker, such as may be determined by the controller 40 determining that the signal, such as a laser signal, received by the receiver exceeds a predefined threshold, the controller may determine that the non-destructive inspection apparatus 22 is properly located relative to the workpiece 24 and may then interrogate the underlying portion of the workpiece. See operation 51 of FIG. 7. The positioning system 44 of this embodiment including the projector may be configured in various manners and, in one embodiment, is configured to illuminate the workpiece 24 with a pattern that defines a plurality of locations to be inspected and, in another embodiment, sequentially illuminates the workpiece with first one marker defining a first location that is interrogated and then another marker following inspection of the workpiece at the first location such that the inspection of the workpiece proceeds from one marker to the next across the workpiece.

The positioning system 44 of one embodiment may include a combination of the the foregoing embodiments including the provision of positioning signals from a plurality of GPS satellites or pseudolites and the illumination of the workpiece 24 by a projector. In this embodiment, the positioning signals from a plurality of GPS satellites or pseudolites may provide for general positioning of the non-destructive inspection apparatus 22 and the illumination of the workpiece 24 by the projector may provide for a finer or more granular level of positioning. While several examples of a positioning system 44 have been provided, the non-destructive inspection apparatus 22 may interact with a variety of different types of positioning systems that identify the location upon the workpiece 24 to be inspected.

Many modifications and other embodiments of the disclosure set forth herein will come to mind to one skilled in the art to which these embodiments pertain having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A non-destructive inspection apparatus comprising:
an ultrasonic sensor configured to be placed in operable contact with a workpiece, wherein the ultrasonic sensor is configured to emit ultrasonic signals into the workpiece and to receive return signals in response to the ultrasonic signals emitted thereby;
a communication interface configured to communicate with a positioning system to identify a location to be inspected, wherein the communication interface is configured to receive a marker indicative of the location to thereafter be inspected in response to the apparatus being aligned with the marker indicative of the location to be inspected; and
a grip operably connected to the ultrasonic sensor such that the grip and the ultrasonic sensor are movable in concert, wherein the grip is configured to support an operator's palm such that force applied to the ultrasonic inspection apparatus by the operator is transferred via the grip to the ultrasonic sensor.

2. A non-destructive inspection apparatus according to claim 1 further comprising a plurality of grips configured to conform to the palm of different respective operators, wherein the plurality of grips are interchangeably connected to the ultrasonic sensor.

3. A non-destructive inspection apparatus according to claim 1 wherein the grip comprises a gel pad configured to conform to the operator's palm.

4. A non-destructive inspection apparatus according to claim 1 wherein the grip comprises at least one input element configured to be actuated by the operator.

5. A non-destructive inspection apparatus according to claim 1 wherein the communication interface is configured to receive positioning signals that define the location of the non-destructive inspection apparatus.

6. A non-destructive inspection apparatus according to claim 1 further comprising a controller configured to determine that the marker received by the communication interface satisfies a predefined threshold so as to be indicative of the apparatus being aligned with the marker.

7. A non-destructive inspection apparatus according to claim 1 wherein the communication interface is configured to receive, following movement of the apparatus, a sequence of markers indicative of different locations to be inspected.

8. A non-destructive inspection apparatus according to claim 1 wherein the ultrasonic sensor is removably attached to the grip such that the ultrasonic sensor is configured to be disengaged from the grip and inserted into another grip.

9. A non-destructive inspection system comprising:
   a non-destructive inspection apparatus comprising:
      an ultrasonic sensor configured to be placed in operable contact with a workpiece, wherein the ultrasonic sensor is configured to emit ultrasonic signals into the workpiece and to receive return signals in response to the ultrasonic signals emitted thereby;
      a communication interface configured to communicate with a positioning system to identify a location to be inspected, wherein the communication interface is configured to receive a marker indicative of the location to thereafter be inspected in response to the apparatus being aligned with the marker indicative of the location to be inspected; and
      a grip operably connected to the ultrasonic sensor such that the grip and the ultrasonic sensor are movable in concert, wherein the grip is configured to support an operator's palm, and wherein the grip comprises at least one input element configured to be actuated by the operator; and
   a computer in communication with the non-destructive inspection apparatus so as to receive information relating to the return signals received by the ultrasonic sensor.

10. A non-destructive inspection system according to claim 9 wherein the grip comprises a plurality of input elements configured to be actuated by the operator.

11. A non-destructive inspection system according to claim 9 wherein the non-destructive inspection apparatus further comprises a plurality of grips configured to conform to the palm of different respective operators, wherein the plurality of grips are interchangeably connected to the ultrasonic sensor.

12. A non-destructive inspection system according to claim 9 wherein the grip comprises a gel pad configured to conform to the operator's palm.

13. A non-destructive inspection apparatus according to claim 9 wherein the communication interface is configured to receive positioning signals that define the location of the non-destructive inspection apparatus.

14. A non-destructive inspection system according to claim 9 further comprising a controller configured to determine that the marker received by the communication interface satisfies a predefined threshold so as to be indicative of the apparatus being aligned with the marker.

15. A non-destructive inspection system according to claim 9 wherein the communication interface is configured to receive, following movement of the apparatus, a sequence of markers indicative of different locations to be inspected.

16. A non-destructive inspection system according to claim 9 wherein the ultrasonic sensor is removably attached to the grip such that the ultrasonic sensor is configured to be disengaged from the grip and inserted into another grip.

17. A method for non-destructively inspecting a workpiece comprising:
   placing an ultrasonic sensor of a non-destructive inspection apparatus in operable contact with the workpiece;
   supporting an operator's palm with a grip that is operably connected to the ultrasonic sensor;
   communicating with a positioning system to identify a location to be inspected, wherein communicating with the positioning system comprises receiving a marker indicative of the location to thereafter be inspected in response to the apparatus being aligned with the marker indicative of the location to be inspected;
   emitting ultrasonic signals from the ultrasonic sensor into the workpiece at the location to be inspected;
   receiving return signals in response to the ultrasonic signals emitted thereby; and
   moving the grip and the ultrasonic sensor in concert in response to force applied to the grip by the operator is transferred via the grip to the ultrasonic sensor.

18. A method according to claim 17 further comprising replacing the grip with another grip configured to conform to the palm of a different operator.

19. A method according to claim 17 wherein the grip comprises an input element, and wherein the method further comprises receiving an indication from the input element regarding actuation of the input element by the operator.

20. A method according to claim 17 wherein communicating with the positioning system comprises receiving positioning signals that define the location of the non-destructive inspection apparatus.

21. A method according to claim 17 further comprising determining that the marker that is received satisfies a predefined threshold so as to be indicative of the apparatus being aligned with the marker.

22. A method according to claim 17 further comprising receiving, following movement of the apparatus, a sequence of markers indicative of different locations to be inspected.

23. A method according to claim 17 further comprising disengaging the ultrasonic sensor from the grip following receipt of the return signals and inserting the ultrasonic sensor into another grip.

* * * * *